United States Patent
Euvrard

Patent Number: 6,155,827
Date of Patent: Dec. 5, 2000

[54] SLEEVE FOR A DENTAL INSTRUMENT

[75] Inventor: Hubert Euvrard, Geneuille, France

[73] Assignee: Micro Mega International Manufactures, S.A., Besancon, France

[*] Notice: This patent issued on a continued prosecution application filed under 37 CFR 1.53(d), and is subject to the twenty year patent term provisions of 35 U.S.C. 154(a)(2).

[21] Appl. No.: 09/028,392

[22] Filed: Feb. 24, 1998

[30] Foreign Application Priority Data

Feb. 19, 1997 [FR] France ................. 97 02131

[51] Int. Cl.⁷ ......................................... A61C 1/18
[52] U.S. Cl. ........................................ 433/133; 433/165
[58] Field of Search ...................... 433/133, 165, 433/166, 125, 114, 126, 127, 128

[56] References Cited

U.S. PATENT DOCUMENTS

| | | | |
|---|---|---|---|
| 1,688,136 | 10/1928 | Chaves et al. | 433/126 |
| 1,875,559 | 9/1932 | Brumm | 433/133 |
| 2,005,849 | 7/1935 | Skinner | 433/133 |
| 2,344,605 | 3/1944 | Droegkamp | 433/133 |
| 2,568,315 | 9/1951 | Björklund | 433/133 |
| 2,813,337 | 11/1957 | Uhler | 433/133 |
| 3,163,934 | 1/1965 | Wiseman | 433/133 |
| 3,368,279 | 2/1968 | Weissman | 433/128 |
| 3,472,045 | 10/1969 | Nelsen et al. | 433/166 |
| 3,751,176 | 8/1973 | Von Hollen | 433/165 |
| 4,014,099 | 3/1977 | Bailey | 433/128 |
| 4,021,920 | 5/1977 | Kirschner et al. | 433/165 |
| 4,285,671 | 8/1981 | Lustig et al. | 433/133 |
| 4,449,932 | 5/1984 | Lustig | 433/133 |
| 4,451,237 | 5/1984 | Filhol | 433/165 |
| 4,478,578 | 10/1984 | Leonard | 433/165 |
| 4,486,175 | 12/1984 | Fisher et al. | 433/133 |
| 4,564,354 | 1/1986 | Rosenstatter | 433/165 |
| 5,007,832 | 4/1991 | Meller et al. | 433/126 |
| 5,040,978 | 8/1991 | Fallon et al. | 433/114 |
| 5,120,220 | 6/1992 | Butler | 433/125 |
| 5,730,595 | 3/1998 | Bailey | 433/126 |

FOREIGN PATENT DOCUMENTS

| | | | |
|---|---|---|---|
| 587856 | 5/1947 | United Kingdom | 433/133 |

*Primary Examiner*—Ralph A. Lewis
*Attorney, Agent, or Firm*—Gary M. Cohen

[57] ABSTRACT

A shank for a dental instrument, including instruments which are used in endodontics and in dental prophylaxis, is fitted on a contra-angle or a handpiece and is provided with a rotary drive which cooperates directly with the rotary transmission members of the kinematic chain of the contra-angle, upstream of the head of the contra-angle. Also, the head of a dental instrument which is equipped with such a shank.

20 Claims, 1 Drawing Sheet

SLEEVE FOR A DENTAL INSTRUMENT

BACKGROUND OF THE INVENTION

The present invention generally relates to the field of dental instrument and more particularly, to shanks which can be fitted on contra-angles or handpieces such as, for example, instruments which are used in endodontics or in dental prophylaxis. The present invention also relates to heads for dental instruments which are equipped with such shanks.

At present, dental instrument shanks intended for use on contra-angles generally conform to the definition given under International Standard ISO 1797, for type 1 shanks.

For rotary driving, a type 1 shank according to ISO 1797 has a flat part which cooperates with an associated shape in the rotating elements of the contra-angle. This combination has the disadvantage of obliging the user, when fitting the instrument on the contra-angle, to seek an appropriate position shank so that the flat part engages the complementary shape of the rotating elements of the contra-angle. In practice, thus is not always easy to do particularly when the user is wearing gloves.

Moreover, the availability of new treatment techniques, particularly in the field of endodontics, has led to the application of greater torques than in the past. This has result in of this is an increased risk of deformation of the flat part, or of breaking of the shank.

In the case of disposable contra-angles, or those with a disposable head (e,g. as are described in the French Patent Application published under No. 2,692,473), the use of a type 1 shank according to standard ISO 1797 has made it necessary to provide a mechanical member in the head of the contra-angle, referred to hereinafter as a "cartridge", for receiving the rotary movement of the kinematic element of the contra-angle. The cartridge receives the shank of the instrument in an axial recess and presents the complementary shape necessary for being driven by the flat part of the shank.

SUMMARY OF THE INVENTION

It is the object of the present invention to remedy these disadvantages. In particular, it is the object of the present invention to provide a shank for a dental instrument which obviates the need to seek an appropriate position for the flat part of the shank (i.e., shank according to standard ISO 1797), which eliminates the risk of the shank breaking on application of a high torque, and which also makes it possible to simplify the construction of the contra-angle which receives the shank (to the extent) that it is no longer necessary to arrange a cartridge in the head of the contra-angle).

These and other objects are achieved in accordance with the present invention by providing a shank for a dental instrument, including instruments which are useful in endodontics and in dental prophylaxis, which can be fitted on a contra-angle or a handpiece and which includes rotary drive means which cooperate directly with the rotary transmission members of the kinematic chain of the contra-angle, upstream of the head of the contra-angle.

Advantageously, the rotary drive means is made unitary with the shank of the dental instrument.

Among other important advantages, the shank of the present invention is provided with surfaces for rotationally guiding the shank in the head of the contra-angle in such a way as to ensure a proper bearing function, and a means for stopping further translation of the shank when fitted in the head of the contra-angle.

BRIEF DESCRIPTION OF THE DRAWINGS

The present invention will be better understood with reference to the following description of a nonlimiting embodiment, together with the attached drawings, in which.

DETAILED DESCRIPTION OF A PREFERRED EMBODIMENT

Figure 1:
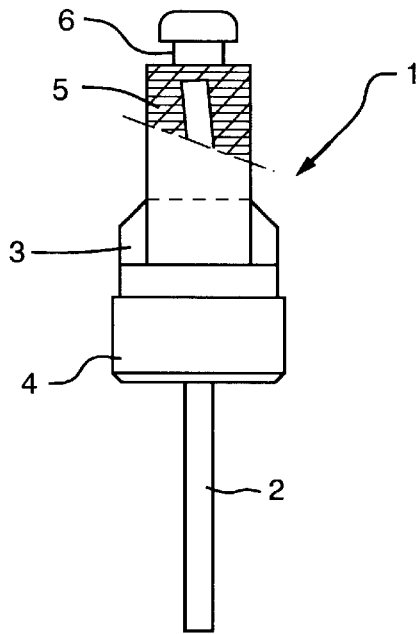
FIG. 1 is a partially sectioned, end elevational view of a shank for a dental instrument produced in accordance with the present invention.

FIG. 1 shows a shank produced according to the invention. In the embodiment shown, the shank (1) is attached to, and receives the active part (2) of the instrument.

It is also possible for the shank and the instrument to be made in such a way as to form only a single piece.

The shank (1) is provided with a rotary drive device which, in the embodiment illustrated, takes the form of a toothed wheel (3) either formed directly in the shank or attached to the shank.

The lower part of the shank (1) includes a first cylindrical part (4) which is used as a rotational guiding surface. To improve rotational guidance, the upper part of the shank (1) is provided with a second cylindrical part (5).

The upper part of the shank is further provided with a groove (6) which operates to receive a means for stopping longitudinal translation following installation (insertion) of the shank, which functions in a manner which is otherwise known per se.

Figure 2:
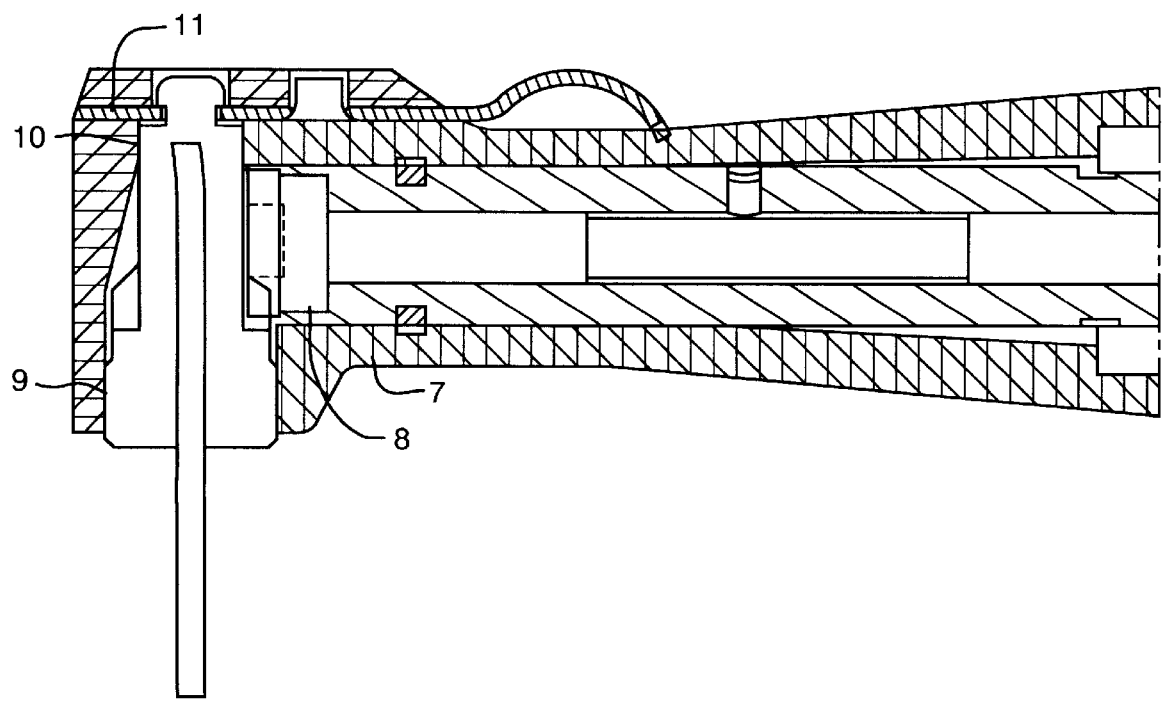
FIG. 2 is a partial, longitudinal cross-sectional view of the dental instrument of FIG. 1, fitted in the head portions of a contra-angle.

FIG. 2 shows the shank of the present invention, fitted in the head (7) of the contra-angle. It will be noted that the head of the contra-angle does not have a cartridge, but rather that the shank cooperates directly with the pinion (8) of the rotational driving means. The surfaces (4) and (5) of the shank cooperate respectively with the surfaces (9) and (10) of the head of the contra-angle to ensure such rotational guidance. The groove (6) of the shank receives the member for stopping, longitudinal translation (11) of the contra-angle head, following installation.

It will be understood that the shank of the present invention can be removably inserted into the head of a dental handpiece or can be fitted on a disposable head, and that such a shank will be well suited to various handpiece heads. In the case of a disposable head, the instrument will not be detachable.

What is claimed is:

1. A combined shank and head for a dental instrument having an active part useful in endodontics and in dental prophylaxis, wherein the head is associated with a contra-angle or a handpiece;

wherein the head includes a cavity for receiving the shank which is open along bottom portions of the head, and an opening defining a guiding surface formed in top portions of the head and in the bottom portions of the head; and wherein the shank is fitted into the opening in the bottom portions of the shank-receiving cavity formed in the head of the contra-angle or the handpiece, and wherein the shank includes;

rotary drive means for directly cooperating with rotary transmission means associated with the contra-angle or the handpiece, wherein the drive means are made unitary with the shank;

a first cylindrical part extending from a first end of the rotary drive means to the active part of the dental instrument and engaging the guiding surface defined by the opening formed in the bottom portions of the head, for rotationally guiding the shank in a lower part of the shank-receiving cavity, wherein the first cylindrical part has a substantially uniform diameter between the first end of the rotary drive means and the active part of the dental instrument; and a second cylindrical part extending from a second end of the rotary drive means opposite to the first end and engaging the guiding surface defined by the opening formed in the top portions of the head, for rotationally guiding the shank in an upper part of the shank-receiving cavity, wherein the second cylindrical part has a substantially uniform diameter which is less than the diameter of the first cylindrical part.

2. The combined shank and head of claim 1 wherein the drive means is a toothed wheel.

3. The combined shank and head of claim 1 wherein the opening formed in the bottom portions of the head has a defined diameter, and wherein the diameter of the first cylindrical part substantially corresponds to the defined diameter of the opening formed in the bottom portions of the head; and wherein the opening formed in the top portions of the head has a defined diameter, and wherein the diameter of the second cylindrical part substantially corresponds to the defined diameter of the opening formed in the top portions of the head.

4. The combined shank and head of claim 3 wherein the first cylindrical part has a first mating surface which engages the guiding surface defined by the opening formed in the bottom portions of the head, and wherein the second cylindrical part has a second mating surface which engages the guiding surface defined by the opening formed in the top portions of the head, so that the shank is guided for rotation within the shank-receiving cavity.

5. The combined shank and head of claim 1 wherein the shank further includes a groove formed in an upper portion of the shank, for receiving means associated with the dental instrument for stopping longitudinal translation of the shank following installation of the shank in the shank-receiving cavity.

6. The combined shank and head of claim 5 wherein the groove of the shank extends fully through the opening formed in the top portions of the head.

7. The combined shank and head of claim 6 wherein the receiving means associated with the dental instrument for stopping the longitudinal translation of the shank following installation of the shank in the shank-receiving cavity includes an arm which terminates in a clamp for engaging the groove, and wherein the arm is pivotally associated with the head so that the clamp is movable into and out of engagement with the groove of the shank which extends through the opening formed in the top portions of the head.

8. The combined shank and head of claim 5 wherein the groove formed in the upper portion of the shank defines a surface for receiving the means associated with the dental instrument for stopping the longitudinal translation of the shank, and wherein the surface has a uniform diameter extending fully along the groove formed in the upper portion of the shank.

9. The combined shank and head of claim 1 wherein the first cylindrical part has a uniform diameter extending fully between the first end of the rotary drive means and the active part of the dental instrument.

10. The combined shank and head of claim 5 wherein the groove is formed integral with the shank.

11. The combined shank and head of claim 1 wherein the shank and the head are made of a disposable material.

12. A combined shank and head for a dental instrument having an active part integral with the shank and useful in endodontics and in dental prophylaxis, wherein the head is associated with a contra-angle or a handpiece;

wherein the head includes a cavity for receiving the shank which is open along bottom portions of the head, an opening defining a guiding surface formed in top portions of the head and in the bottom portions of the head, and clamping means for stopping longitudinal translation of the shank following installation of the shank in the shank-receiving cavity; and wherein the shank is fitted into the opening in the bottom portions of the shank-receiving cavity formed in the head of the contra-angle or the handpiece, and wherein the shank includes;

rotary drive means for directly cooperating with rotary transmission means associated with the contra-angle or the handpiece, wherein the drive means are made unitary with the shank;

a first cylindrical part extending from a first end of the rotary drive means to the active part of the dental instrument and engaging the guiding surface defined by the opening formed in the bottom portions of the head, for rotationally guiding the shank in a lower part of the shank-receiving cavity, wherein the first cylindrical part has a substantially uniform diameter between the first end of the rotary drive means and the active part of the dental instrument;

a second cylindrical part extending from a second end of the rotary drive means opposite to the first end and engaging the guiding surface defined by the opening formed in the top portions of the head, for rotationally guiding the shank in an upper part of the shank-receiving cavity, wherein the second cylindrical part has a substantially uniform diameter which is less than the diameter of the first cylindrical part; and a groove formed in an upper portion of the shank, for receiving the clamping means associated with the head, wherein the groove is made unitary with the shank.

13. The combined shank and head of claim 12 wherein the drive means is a toothed wheel.

14. The combined shank and head of claim 12 wherein the opening formed in the bottom portions of the head has a defined diameter, and wherein the diameter of the first cylindrical part substantially corresponds to the defined diameter of the opening formed in the bottom portions of the head; and wherein the opening formed in the top portions of the head has a defined diameter, and wherein the diameter of the second cylindrical part substantially corresponds to the defined diameter of the opening formed in the top portions of the head.

15. The combined shank and head of claim 14 wherein the first cylindrical part has a first mating surface which engages the guiding surface defined by the opening formed in the bottom portions of the head, and wherein the second cylindrical part has a second mating surface which engages the guiding surface defined by the opening formed in the top portions of the head, so that the shank is guided for rotation within the shank-receiving cavity.

16. The combined shank and head of claim 12 wherein the shank and the head are made of a disposable material.

17. The combined shank and head of claim 12 wherein the groove of the shank extends fully through the opening formed in the top portions of the head.

18. The combined shank and head of claim 17 wherein the receiving means associated with the dental instrument for stopping the longitudinal translation of the shank following installation of the shank in the shank-receiving cavity includes an arm which terminates in a clamp for engaging the groove, and wherein the arm is pivotally associated with the head so that the clamp is movable into and out of engagement with the groove of the shank which extends through the opening formed in the top portions of the head.

19. The combined shank and head of claim 12 wherein the groove formed in the upper portion of the shank defines a surface for receiving the means associated with the dental instrument for stopping the longitudinal translation of the shank, and wherein the surface has a uniform diameter extending fully along the groove formed in the upper portion of the shank.

20. The combined shank and head of claim 12 wherein the first cylindrical part has a uniform diameter extending fully between the first end of the rotary drive means and the active part of the dental instrument.

* * * * *